United States Patent
Hillbratt et al.

(10) Patent No.: US 10,616,695 B2
(45) Date of Patent: Apr. 7, 2020

(54) EXECUTION AND INITIALISATION OF PROCESSES FOR A DEVICE

(71) Applicant: Cochlear Limited, Macquarie University, NSW (AU)

(72) Inventors: Martin Evert Gustaf Hillbratt, Molnlycke (SE); Kristian Gunnar Asnes, Molnlycke (SE)

(73) Assignee: Cochlear Limited, Macquarie University, NSW (AU)

( * ) Notice: Subject to any disclaimer, the term of this patent is extended or adjusted under 35 U.S.C. 154(b) by 688 days.

(21) Appl. No.: 15/158,347

(22) Filed: May 18, 2016

(65) Prior Publication Data

US 2017/0289705 A1    Oct. 5, 2017

Related U.S. Application Data

(60) Provisional application No. 62/317,293, filed on Apr. 1, 2016.

(51) Int. Cl.
*H04R 25/00* (2006.01)
*A61N 1/36* (2006.01)
*A61N 1/372* (2006.01)

(52) U.S. Cl.
CPC ....... *H04R 25/453* (2013.01); *A61N 1/36038* (2017.08); *A61N 1/37223* (2013.01);
(Continued)

(58) Field of Classification Search
CPC ...... H04R 25/45–507; H04R 25/00–75; H04R 2225/00–83; H04R 2460/00–17
See application file for complete search history.

(56) References Cited

U.S. PATENT DOCUMENTS

2005/0226446 A1* 10/2005 Luo .................. H04R 25/00
                                                         381/312
2006/0222194 A1   10/2006 Bramslow et al.
(Continued)

FOREIGN PATENT DOCUMENTS

JP     09-327097       12/1997
WO    2015183263 A1    12/2015

OTHER PUBLICATIONS

International Search Report and Written Opinion for PCT/IB2017/000414, dated Jul. 10, 2017, 10 pages.
(Continued)

*Primary Examiner* — Thaddeus B Cox
(74) *Attorney, Agent, or Firm* — Pilloff Passino & Cosenza LLP; Martin J. Cosenza

(57) ABSTRACT

Systems and methods for detecting when a device is placed into an operational position are disclosed. Upon determination that the device is in the operational position, one or more processes can be executed. Execution or initialization of the processes upon detection of the operational position provides for the determination of optimal settings than would otherwise be determined if the processes automatically executed before detection of the operational position. Further aspects of the present disclosure relate to determining when the device is no longer in an operational position upon which time the execution of the processes are terminated. The settings in place upon termination can be saved and reapplied the next time the device is in the operational position.

31 Claims, 10 Drawing Sheets

(52) U.S. Cl.
CPC ......... *H04R 25/407* (2013.01); *H04R 25/554* (2013.01); *H04R 25/606* (2013.01); *H04R 25/70* (2013.01); *H04R 2225/61* (2013.01); *H04R 2225/67* (2013.01); *H04R 2460/13* (2013.01)

(56) References Cited

U.S. PATENT DOCUMENTS

| | | | |
|---|---|---|---|
| 2009/0202091 A1 | 8/2009 | Pedersen et al. | |
| 2011/0158443 A1* | 6/2011 | snes | H04R 25/606 381/326 |
| 2012/0082329 A1* | 4/2012 | Neumeyer | H04R 25/50 381/314 |
| 2012/0197345 A1* | 8/2012 | Staller | A61B 5/7475 607/57 |
| 2014/0126731 A1* | 5/2014 | Litvak | H04R 25/305 381/60 |
| 2014/0126759 A1* | 5/2014 | Rasmussen | H04R 25/55 381/315 |
| 2014/0185813 A1 | 7/2014 | Ozden et al. | |
| 2014/0321682 A1 | 10/2014 | Kofod-Hansen et al. | |
| 2014/0330160 A1* | 11/2014 | Sohn, II | H04R 25/305 600/559 |
| 2014/0348360 A1 | 11/2014 | Gran | |
| 2014/0363036 A1* | 12/2014 | Hillbratt | H04R 25/45 381/318 |
| 2015/0230036 A1 | 8/2015 | Pedersen et al. | |
| 2017/0143962 A1* | 5/2017 | Mishra | H04R 25/505 |

OTHER PUBLICATIONS

Extended European search report for European Patent Application No. 17 773 373.0, dated Oct. 14, 2019.

\* cited by examiner

EXECUTION AND INITIALISATION OF PROCESSES FOR A DEVICE

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Aspects of the present disclosure relate to systems and methods for detecting when a medical device is placed into an operational position on a recipient. Upon determination that the device is in the operational position, one or more processes can be executed. Execution of the processes upon detection of the operational position provides for the determination of optimal settings than would otherwise be determined if the processes automatically executed upon device initialization. Further aspects of the present disclosure relate to determining when the device is no longer in an operational position upon which time the execution of the processes are terminated. The settings in place upon termination can be saved and reapplied the next time the device is in the operational position.

Further aspects of the present disclosure relate to a feedback algorithm that reduces the likelihood of generating audible artefacts. In examples, the feedback algorithm executes with an initial phase that employs a faster adaptation speed. During the initial phase, the amplitude of the device may be incrementally increased. Upon completion of the initial phase, the feedback algorithm may be adjusted to employ an operational adaptation speed.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
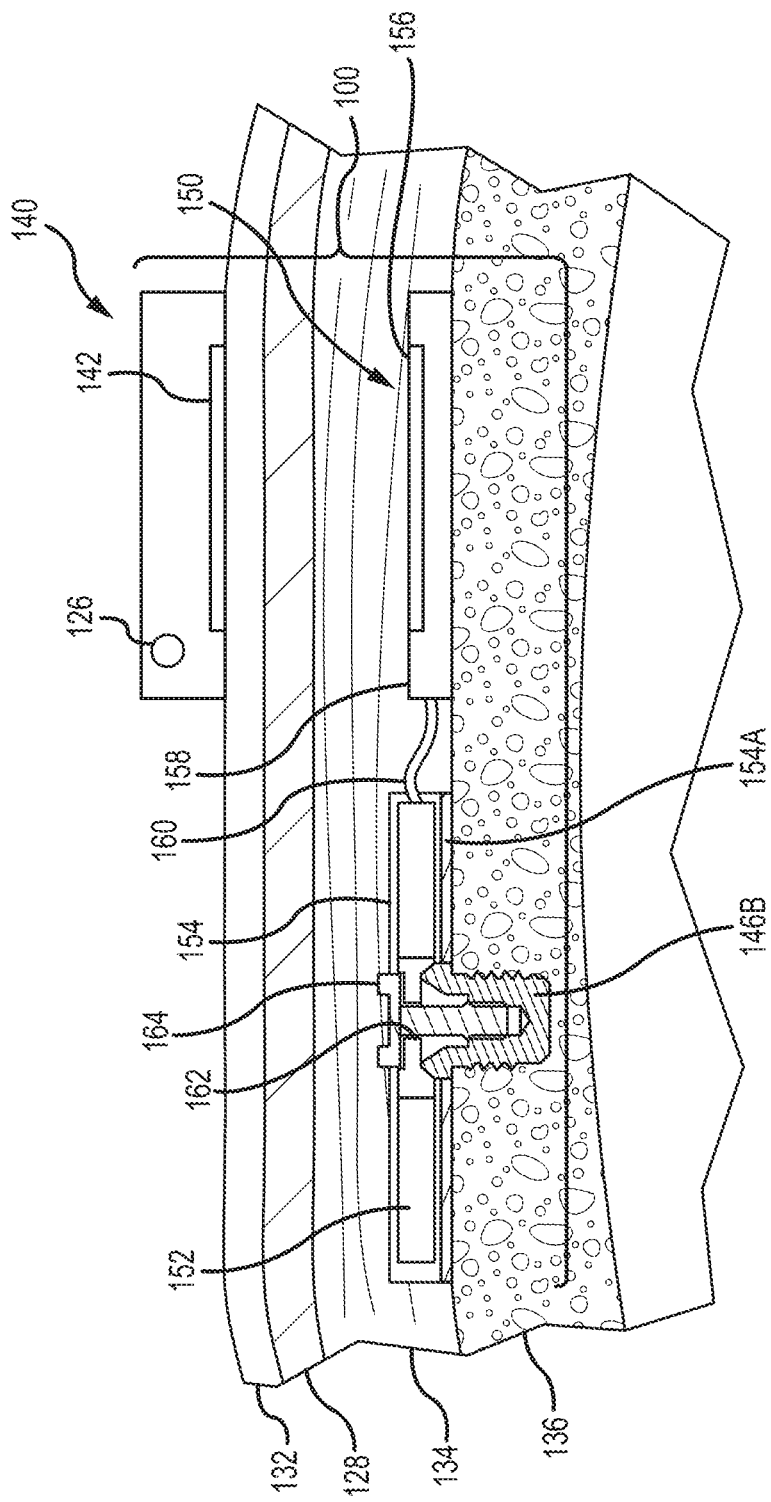
FIG. 1 depicts a partial cross-sectional schematic view of an active transcutaneous bone conduction device worn on a recipient.

Various types of devices, such as medical devices that operate on and/or within a recipient or such as consumer electronic devices that generate or assist in generation of audible output, utilize processes that execute after the devices are turned on and that could execute before the devices are put into the location or one of the locations the devices are intended to operate in (e.g., an operational position), but that operate more effectively and/or efficiently when executed after the devices or one or more components of the devices are put into an operational position. Non-limiting examples of such processes including beam forming and feedback algorithms. The operation of such processes is effectible by a position of the devices or one or more components of the devices.

For instance, many recipients of auditory prostheses can experience discomfort during initialization of the auditory prosthesis. The discomfort can be the result of audible artifacts that are generated during the establishment of a stable feedback loop for the auditory prosthesis. Feedback is a major concern when increasing gain in any system with a microphone or similar sensor in the vicinity of the output transducer. Problematic feedback occurs when the gain (i.e., amplitude) of the device is larger than the attenuation in the feedback loop outside the device, i.e., a negative remaining gain margin, which is often the state of an auditory prosthesis during initialization of the device.

One common method to reduce feedback is to identify when feedback occurs and cancel out the feedback signal with an adaptive filter in a feedback algorithm. Some pre-filtering or other start point criteria are often used to adapt faster with less audible artefacts. In existing systems, a feedback algorithm is executed as soon as an auditory prosthesis is initialized and before it is placed in an operational position. For example, auditory prostheses are generally initialized while still in a recipient's hand and then subsequently placed in an operational position, e.g., on the recipient's head, within the recipient's ear, etc. However, because the establishment of the feedback loop is performed while an auditory prosthesis (in its entirety) or a component of the auditory prosthesis, e.g., a sound processor, is in the recipient's hand, the established feedback loop is not optimally set for operational performance. This results in a sub-optimal result and/or a sub-optimal experience, e.g., audible artefacts.

For instance, when a feedback algorithm is first initialized, the adaptation speed of the feedback algorithm can be set to an aggressive, e.g., quicker, speed. The aggressive adaptation speed can result in the generation of audible artifacts, e.g., chirps or tones, that can cause discomfort or embarrassment to a recipient.

Aspects of the present disclosure relate to detecting when a component of an auditory prosthesis, e.g., an external device for an implantable prosthesis, a hearing aid, etc., is placed in an operational position for the recipient. Upon detection of the placement, a feedback algorithm having a faster initial adaptation speed is executed for a limited time. In this way the auditory prosthesis adapts to address, e.g., changes within the recipient, where a portion of the feedback path exists in some embodiments, since the auditory prosthesis was fitted to the recipient and/or was last in an operational position. A result is determination of optimal operational settings. In embodiments, in order to reduce the likelihood of audible artefacts, the initial feedback algorithm is performed during a ramp up of volume (e.g., gain or amplitude) which allows the feedback algorithm to adapt before high gain introduces a feedback problem.

Additional embodiments relate to initialization settings based on a feedback measurement setting, for example using a pre-filter or allowing the adaptive feedback algorithm to start from a previously determined feedback setting, for example using frequency based upon air delay, filter dynamics, step size, etc. In doing so, the difference between the initialization settings and any changes to the feedback path since the initial fitting of the auditory prosthesis will be reduced, thereby allowing for the use of a slower adaptation speed during an initialisation stage. A slower adaptation speed reduces the likelihood of instability and/or audible artefacts, thereby enhancing the recipient's experience. For instance, settings can be smoothed and/or averaged over time. In alternative embodiments, samples of the filter settings are saved during this first initialization time and an averaged filter is then used as starting point for the adaptive filter during a subsequent initialization.

Various devices that can employ and benefit from the systems and methods disclosed herein will now be described. While specific devices are described herein, one of skill in the art will appreciate that other types of devices can employ the aspects disclosed herein without departing from the scope of this disclosure. For instance, the type of processes executed upon placement of an auditory prosthesis in an operational position can vary depending on the type of the auditory prosthesis. Some types of auditory prostheses, such as certain cochlear implants, do not have problems with feedback, but do utilize beam forming algorithms. Like feedback algorithms, beam forming algorithms are best initialized while the device executing such is set in an operational position. Other auditory prostheses (e.g., traditional hearing aids, bone conduction devices, direct acoustic stimulators, middle ear devices, electro-acoustic implants, etc.), do have problems with feedback and some utilize beam forming algorithms. Such devices ideally initialize feedback and beamforming algorithms while the auditory prostheses, or a component of the auditory prosthesis, is set in an operational position, as described herein.

FIG. 1 depicts a partial cross-sectional schematic view of an active transcutaneous bone conduction device 100 worn on a recipient. The active transcutaneous bone conduction device 100 includes an external device 140 and an implantable component 150. The bone conduction device 100 of FIG. 1 is an active transcutaneous bone conduction device in that the vibrating actuator 152 is located in the implantable component 150. Specifically, a vibratory element in the form of vibrating actuator 152 is located in an encapsulant 154 of the implantable component 150. In the various examples described herein, implanted encapsulants 154 can be biocompatible ceramic, plastic, or other materials. In an example, much like the vibrating actuator 152 described below with respect to transcutaneous bone conduction devices, the vibrating actuator 152 is a device that converts electrical signals into vibration.

External component 140 includes a sound input element 126 that converts sound into electrical signals. Specifically, the transcutaneous bone conduction device 100 provides these electrical signals to a sound processor (not shown) that processes the electrical signals, and then provides those processed signals to the implantable component 150 through the skin 132, fat 128, and muscle 134 of the recipient via a magnetic inductance link. In this regard, a transmitter coil 142 of the external component 140 transmits these signals to implanted receiver coil 156 located in an encapsulant 158 of the implantable component 150. Successful communications between transmitter coil 142 and receiver coil 156 can be indicative of the external component 140 being in an operational position (and in some embodiments, trigger, e.g., a 'coil-on' alert). If the coils are too far apart, too misaligned, shifted, etc., such successful communications are not possible. The margin for error in terms of placement of the transmitter coil 142 of the external component 140 in relation to the implanted receiver coil 156 depends on the characteristics of a given device.

The vibrating actuator 152 converts the electrical signals into vibrations. In another example, signals associated with external sounds can be sent to an implanted sound processor disposed in the encapsulant 158, which then generates electrical signals to be delivered to vibrating actuator 152 via electrical lead assembly 160. The vibrating actuator 152 is mechanically coupled to the encapsulant 154. Encapsulant 154 and vibrating actuator 152 collectively form a vibrating element. The encapsulant 154 is substantially rigidly attached to bone fixture 146B, which is secured to bone 136. A silicone layer 154A can be disposed between the encapsulant 154 and the bone 136. In this regard, encapsulant 154 includes through hole 162 that is contoured to the outer contours of the bone fixture 146B. Screw 164 is used to secure encapsulant 154 to bone fixture 146B. As a result of the screw 164 and the bone fixture 146B, the vibrating actuator 152 maintains a relatively stable position in relation to the recipient's head. As result of this relatively stable position, portions of the feedback path within the recipient are relatively consistent between cycles of operation of the active transcutaneous bone conduction device 100. Less stable locational relationships between an actuator and a recipient might be found for other types of auditory prostheses, such as hearing aids and passive transcutaneous bone conduction devices, which could negatively impact beam forming and/or feedback algorithms.

Figure 2:
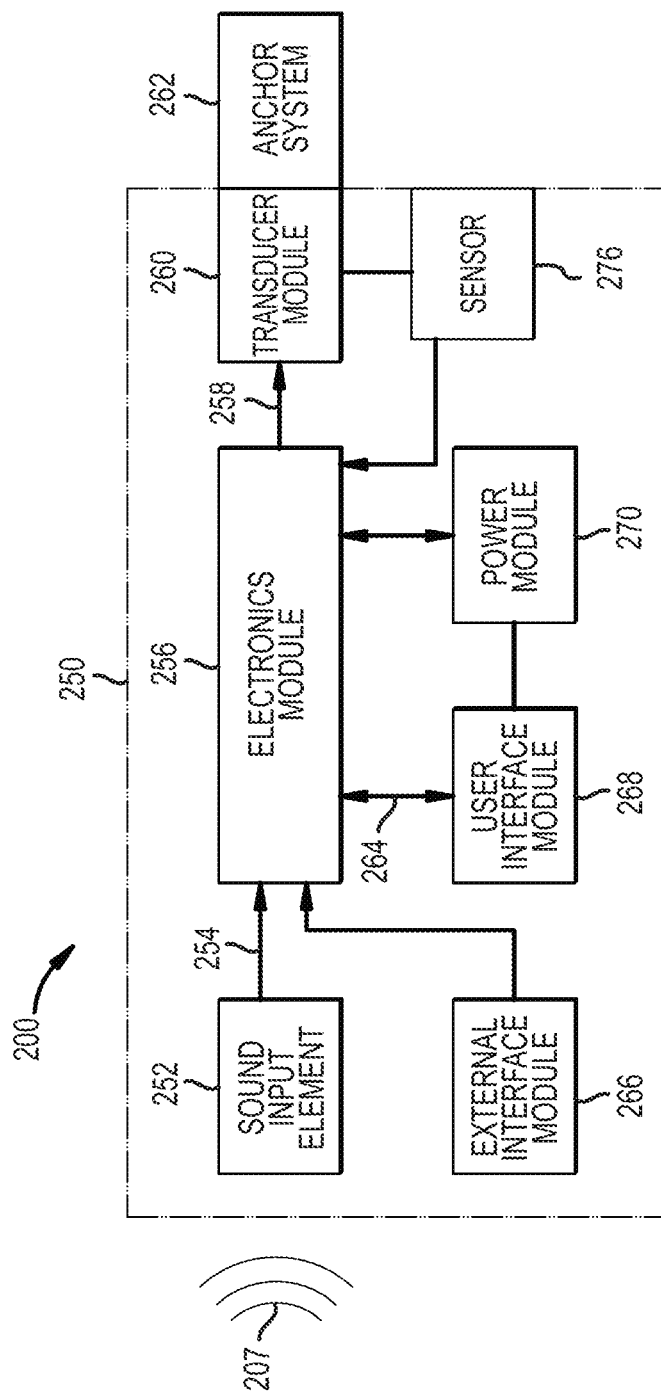
FIG. 2 is a schematic diagram of a percutaneous bone conduction device.

FIG. 2 is a schematic diagram of a percutaneous bone conduction device 200. Sound 207 is received by sound input element 252. In some arrangements, sound input element 252 is a microphone configured to receive sound 207, and to convert sound 207 into electrical signal 254. Alternatively, sound 207 is received by sound input element 252 as an electrical signal. As shown in FIG. 2, electrical signal 254 is output by sound input element 252 to electronics module 256. Electronics module 256 is configured to convert electrical signal 254 into adjusted electrical signal 258. As described below in more detail, electronics module 256 can include a sound processor, control electronics, transducer drive components, and a variety of other elements.

As shown in FIG. 2, transducer 260 receives adjusted electrical signal 258 and generates a mechanical output force in the form of vibrations that is delivered to the skull of the recipient via anchor system 262, which is coupled to bone conduction device 200. Delivery of this output force causes motion or vibration of the recipient's skull, thereby activating the hair cells in the recipient's cochlea (not shown) via cochlea fluid motion. A power module 270 provides electrical power to one or more components of bone conduction device 200. For ease of illustration, power module 270 has been shown connected only to user interface module 268 and electronics module 256. However, it should be appreciated that power module 270 can be used to supply power to any electrically powered circuits/components of bone conduction device 200.

User interface module 268, which is included in bone conduction device 200, allows the recipient to interact with bone conduction device 200. For example, user interface module 268 can allow the recipient to adjust the volume, alter the speech processing strategies, power on/off the device, etc. In the example of FIG. 2, user interface module 268 communicates with electronics module 256 via signal line 264.

Bone conduction device 200 can further include external interface module 266 that can be used to connect electronics module 256 to an external device, such as a fitting system. Using external interface module 266, the external device, can obtain information from the bone conduction device 200 (e.g., the current parameters, data, alarms, etc.), and/or modify the parameters of the bone conduction device 200 used in processing received sounds and/or performing other functions.

In the example of FIG. 2, sound input element 252, electronics module 256, transducer 260, power module 270, user interface module 268, and external interface module 266 have been shown as integrated in a single housing, referred to as an auditory prosthesis housing or an external portion housing 250. However, it should be appreciated that in certain examples, one or more of the illustrated components can be housed in separate or different housings. Similarly, it should also be appreciated that in such examples, direct connections between the various modules and devices are not necessary and that the components can communicate, for example, via wireless connections. Additionally, the bone conduction device 200 can include a sensor 276 that can be used to detect when the device 200 is in an operational position on the recipient. For example, the sensor 276 can detect the presence of a corresponding emitter (RFID, Bluetooth, Wi-Fi, etc.) located on the anchor system 262. Alternatively, the sensor 276 can detect a condition of the transducer module 260 (e.g., the load on the transducer module) indicative of that component being engaged with the anchor system 262. Such detection can then be communicated to the electronics module 256 that the device is in an operational position. The sensor 276 can also be a proximity or position sensor, or may be a button, switch, or other mechanical element that can detect a connection between the transducer module 260 and the anchor system 262.

Typically, the external portion housing 250 is attached to the anchor system 262 in a relatively rigid manner via a so called snap coupling. When in operation, the external portion housing 250 is snapped to the anchor system 262. As a result of this attachment, the external portion housing 250 (and the actuator or vibrator contained therein) maintains a relatively stable position in relation to the recipient's head, e.g., the external portion housing 250 is prevented from shifting during operation and from one cycle of operation to the next. As result of this relatively stable position, portions of the feedback path are relatively consistent between cycles of operation of the percutaneous bone conduction device 200. Less stable locational relationships might be found for other types of auditory prostheses, such as hearing aids and passive transcutaneous bone conduction devices. Note however that in some such embodiments, the external portion housing 250 is able to rotate about an axis of the anchor system 262. That is to stay that at the start of each cycle of operation, the external portion housing 250 might be rotated more or less (in relation to a hypothetical zero degrees of rotation) than in the previous cycle of operation, which can have in impact or beam forming algorithms, particularly the initialization of the beam forming algorithm.

Figure 3:
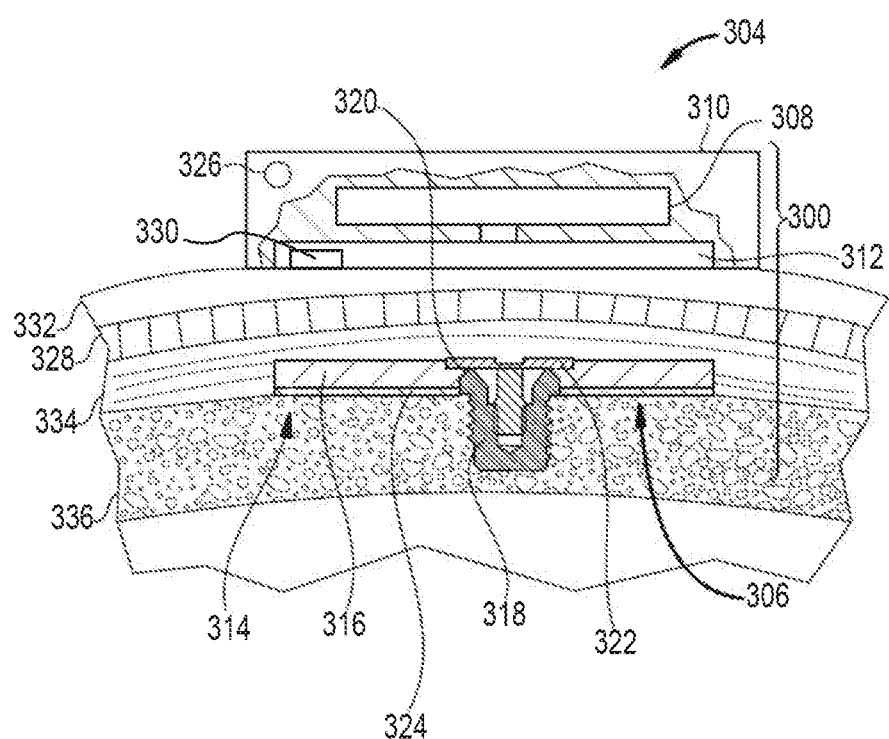
FIG. 3 depicts a partial cross-sectional schematic view of a passive transcutaneous bone conduction device worn on a recipient.

FIG. 3 depicts an example of a passive transcutaneous bone conduction device 300 that includes an external portion 304 and an implantable portion 306. The device 300 of FIG. 3 is a passive transcutaneous bone conduction device in that a vibrating actuator 308 is located in the external portion 304. In such devices, there are typically no active electrical or mechanical components in the implanted portion 306.

Vibrating actuator 308 is located in housing 310 of the external component, and is coupled to a pressure or transmission plate 312. The pressure plate 312 can be in the form of a permanent magnet and/or in another form that generates and/or is reactive to a magnetic field, or otherwise permits the establishment of magnetic attraction between the external portion 304 and the implantable portion 306 sufficient to hold the external portion 304 against the skin of the recipient. Magnetic attraction can be further enhanced by utilization of a magnetic implantable plate 316 that is secured to the bone 336. Single magnets are depicted in FIG. 3. In alternative examples, multiple magnets in both the external portion 304 and implantable portion 306 can be utilized. In a further alternative example the pressure plate 312 can include an additional plastic or biocompatible encapsulant (not shown) that encapsulates the pressure plate 312 and contacts the skin 332 of the recipient. The device 300 may include a sensor or other component 330, such as those described above, so as to detect when the device 300 is in an operational position. These sensors or components 330 can, e.g., detect RFID, Bluetooth, or WiFi emitted from an implantable portion 306. Alternatively, the sensor 330 can detect a magnetic field indicative of the device 300 being in an operational position. In another example, the sensor 330 can be a button or mechanical switch or structure that is depressed when the device 300 is in contact with the skin 332. The sensor 330 may also be disposed within the device 300, discrete from the plate, and detect a load condition on the vibrating actuator 308 that is indicative of the pressure plate 312 being in contact with the skin 332. In the illustrated embodiment of FIG. 3, the sensor 330 is disposed on the pressure plate 312, but in other embodiments, the sensor 330 is disposed elsewhere, such as elsewhere within the device 300.

In an example, the vibrating actuator 308 is a device that converts electrical signals into vibration. In operation, sound input element 326 converts sound into electrical signals. Specifically, the transcutaneous bone conduction device 300 provides these electrical signals to vibrating actuator 308, via a sound processor (not shown) that processes the electrical signals, and then provides those processed signals to vibrating actuator 308. The vibrating actuator 308 converts the electrical signals into vibrations. Because vibrating actuator 308 is mechanically coupled to pressure plate 312, the vibrations are transferred from the vibrating actuator 308 to pressure plate 312. Implantable plate assembly 314 is part of the implantable portion 306, and can be made of a ferromagnetic material that can be in the form of a permanent magnet. The implantable portion 306 generates and/or is reactive to a magnetic field, or otherwise permits the establishment of a magnetic attraction between the external portion 304 and the implantable portion 306 sufficient to hold the external portion 304 against the skin 332 of the recipient. Accordingly, vibrations produced by the vibrating actuator 308 of the external portion 304 are transferred from pressure plate 312 to implantable plate 316 of implantable plate assembly 314. This can be accomplished as a result of mechanical conduction of the vibrations through the skin 332, resulting from the external portion 304 being in direct contact with the skin 332 and/or from the magnetic field between the two plates 312, 316. These vibrations are typically transferred without a component penetrating the skin 332, fat 328, or muscular 334 layers on the head.

As can be seen, the implantable plate assembly 314 is substantially rigidly attached to bone fixture 318 in this example. Implantable plate assembly 314 includes through hole 320 that is contoured to the outer contours of the bone fixture 318, in this case, a bone fixture 318 that is secured to the bone 336 of the skull. This through hole 320 thus forms a bone fixture interface section that is contoured to the exposed section of the bone fixture 318. In an example, the sections are sized and dimensioned such that at least a slip fit or an interference fit exists with respect to the sections. Plate screw 322 is used to secure implantable plate assembly 314 to bone fixture 318. As can be seen in FIG. 3, the head of the plate screw 322 is larger than the hole through the implantable plate assembly 314, and thus the plate screw 322 positively retains the implantable plate assembly 314 to the bone fixture 318. In certain examples, a silicon layer 324 is located between the implantable plate 316 and bone 336 of the skull.

But while implantable components of the passive transcutaneous bone conduction device 300 are relatively rigidly fixed to the skull of the recipient, the external components can rotate during and between cycles of operation of the passive transcutaneous bone conduction device 300. The external components can also shift as they are typically not, e.g., snapped in to place during operation. This rotation and/or shifting can impact operation of, e.g., beam forming algorithms and feedback algorithms.

Figure 4:
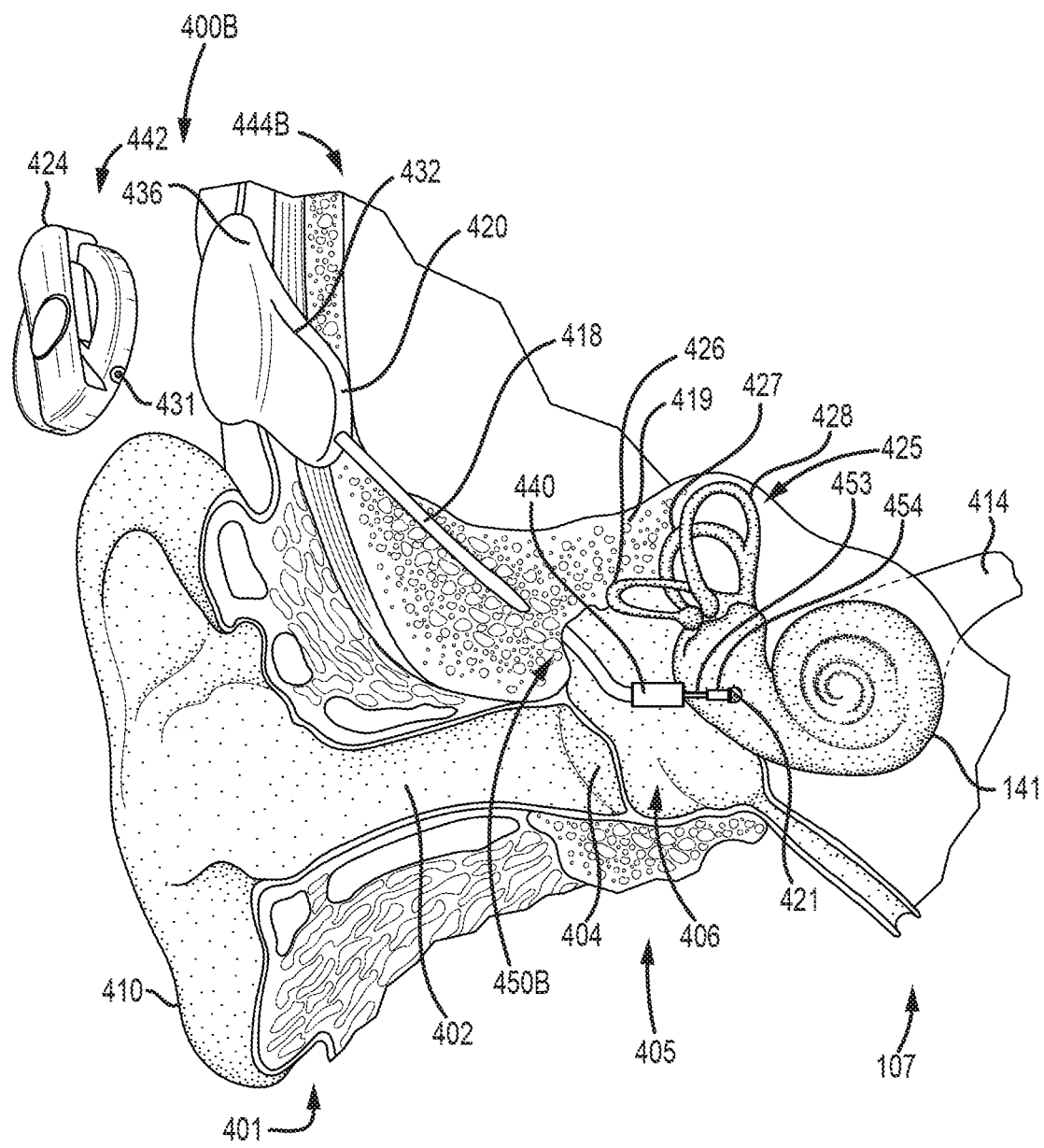
FIG. 4 is a partial view of a direct acoustic stimulator worn on a recipient.

FIG. 4 is a perspective view of a direct acoustic stimulator 400B, comprising an external component 442 which is directly or indirectly attached to the body of the recipient, and internal component 444B which is implanted in the recipient. The recipient has an outer ear 401, a middle ear 405 and an inner ear 407. Components of outer ear 401, middle ear 405 and inner ear 407 are described below. In a fully functional ear, outer ear 401 comprises an auricle 410 and an ear canal 402. An acoustic pressure or sound wave is collected by auricle 410 and channeled into and through ear canal 402. Disposed across the distal end of ear canal 402 is a tympanic membrane 404 which vibrates in response to the sound wave. This vibration is coupled to oval window or fenestra ovalis (not shown) through three bones of middle ear 405, collectively referred to as the ossicles. Bones of middle ear 405 serve to filter and amplify the sound wave, causing the oval window to articulate, or vibrate in response to vibration of tympanic membrane 404. This vibration sets up waves of fluid motion of the perilymph within cochlea 441. Such fluid motion, in turn, activates tiny hair cells (not shown) inside of cochlea 441. Activation of the hair cells causes appropriate nerve impulses to be generated and transferred through the spiral ganglion cells (not shown) and auditory nerve 414 to the brain (also not shown) where they are perceived as sound.

External component 442 typically comprises one or more sound input elements, such as microphones 431, sound processing unit 424, a power source (not shown), and an external transmitter unit (also not shown). The internal component 444B comprises internal receiver unit 432, stimulator unit 420, and stimulation arrangement 450B. Stimulation arrangement 450B is implanted in middle ear 405 and includes actuator 440, stapes prosthesis 454 and coupling element 453 connecting the actuator 440 to the stapes prosthesis 454. In this example, stimulation arrangement 450B is implanted and/or configured such that a portion of stapes prosthesis 454 abuts round window 421. It should be appreciated that stimulation arrangement 450B can alternatively be implanted such that stapes prosthesis 454 abuts an opening in horizontal semicircular canal 426, in posterior semicircular canal 427 or in superior semicircular canal 428.

A sound signal is received by one or more microphones 424, processed by sound processing unit 426, and transmitted as encoded data signals to internal receiver 432. Based on these received signals, stimulator unit 420 generates drive signals that cause actuation of actuator 440. This actuation is transferred to stapes prosthesis 454 such that a wave of fluid motion is generated in the perilymph in scala tympani. Such fluid motion, in turn, activates the hair cells of the organ of Corti. Activation of the hair cells causes appropriate nerve impulses to be generated and transferred through the spiral ganglion cells (not shown) and auditory nerve 414 to the brain (also not shown) where they are perceived as sound.

FIG. 4 provides an illustrative example of a direct acoustic stimulator system, more specifically, a direct acoustic cochlear stimulator. A middle ear mechanical stimulation device (or middle ear device) can be configured in a similar manner, with the exception that instead of the actuator 440 being coupled to the inner ear of the recipient, the actuator is coupled to a bone of the middle ear 405. For example, the actuator can stimulate the middle ear by direct mechanical coupling via a coupling element (e.g., similar to coupling element 453).

Figure 5:
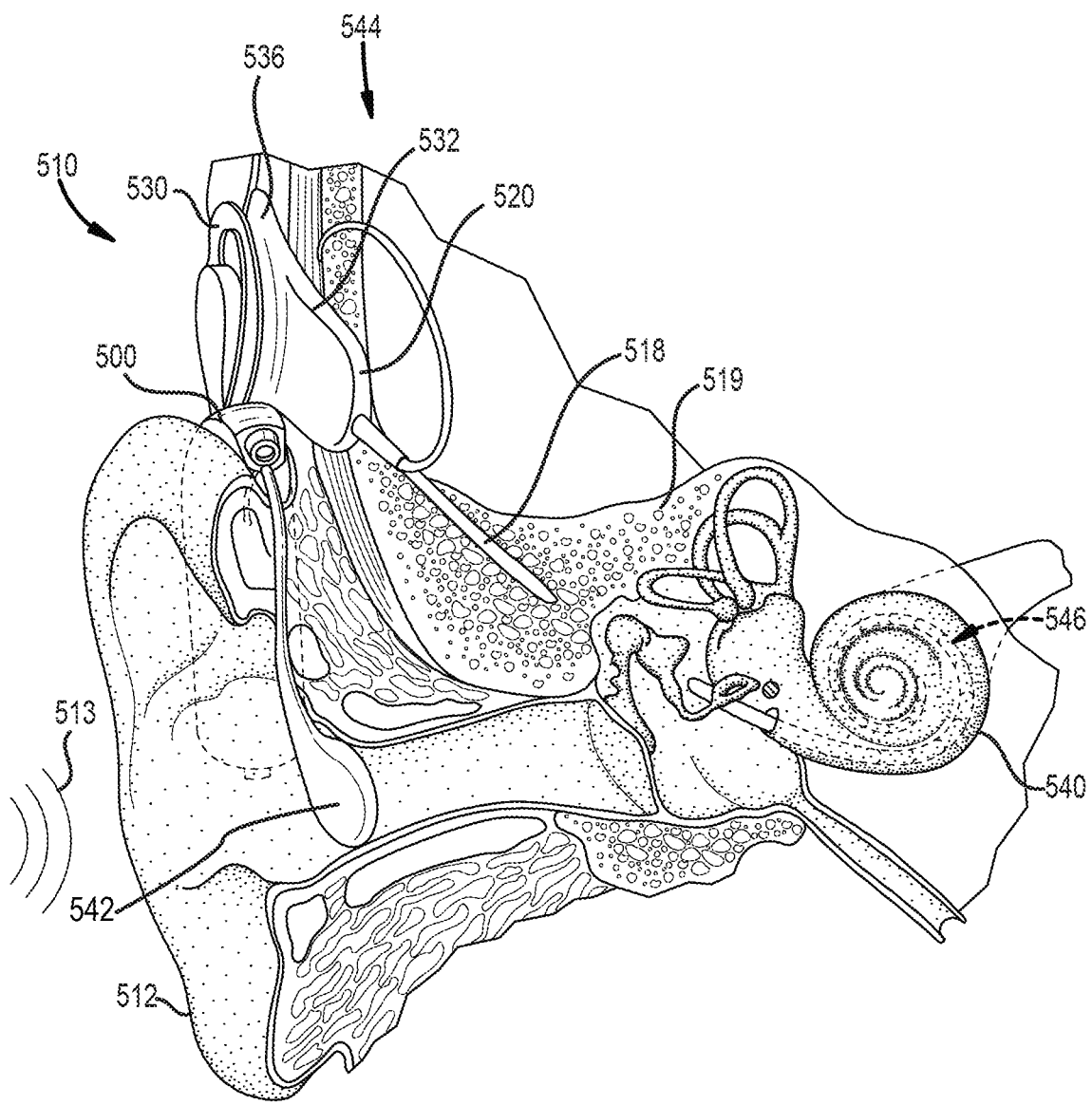
FIG. 5 is a partial view of a behind-the-ear auditory prosthesis worn on a recipient.

Referring to FIG. 5, cochlear implant system 500 includes an implantable component 544 typically having an internal receiver/transceiver unit 532, a stimulator unit 520, and an elongate lead 518. The internal receiver/transceiver unit 532 permits the cochlear implant system 510 to receive and/or transmit signals to an external device. The external device can be a button sound processor worn on the head that includes a receiver/transceiver coil and sound processing components. Alternatively, the external device can be just a receiver/transceiver coil in communication with a BTE device that includes the sound processing components and microphone. The implantable component 544 includes an internal coil 536, and preferably, a magnet (not shown) fixed relative to the internal coil 536. The magnet is embedded in a pliable silicone or other biocompatible encapsulant, along with the internal coil 536. Signals sent generally correspond to external sound 513. Internal receiver unit 532 and stimulator unit 520 are hermetically sealed within a biocompatible housing, sometimes collectively referred to as a stimulator/receiver unit. The magnets facilitate the operational alignment of the external and internal coils, enabling internal coil 536 to receive power and stimulation data from external coil 530. The external coil 530 is contained within an external portion 550. Elongate lead 518 has a proximal end connected to stimulator unit 520, and a distal end implanted in cochlea 540. Elongate lead 518 extends from stimulator unit 520 to cochlea 540 through mastoid bone 519. An intracochlear region 546 extends from the lead 518 and into the cochlea 540.

In certain examples, external coil 530 transmits electrical signals (e.g., power and stimulation data) to internal coil 536 via a radio frequency (RF) link, as noted above. Internal coil 536 is typically a wire antenna coil comprised of multiple turns of electrically insulated single-strand or multi-strand platinum or gold wire. The electrical insulation of internal coil 536 is provided by a flexible silicone molding. Various types of energy transfer, such as infrared (IR), electromagnetic, capacitive and inductive transfer, can be used to transfer the power and/or data from external device to cochlear implant. Communication of the signals between the external coil 530 and the internal induction coil 536 can be indicative of the external device 530 being in an operational position. Certain cochlear implant systems 500 can also include a speaker 542 that extends into an ear canal of a recipient so as to deliver audible sounds at certain predetermined frequencies. Such devices, referred to as electro-acoustic implants, can also benefit from the technologies described herein to reduce feedback.

Figure 6:
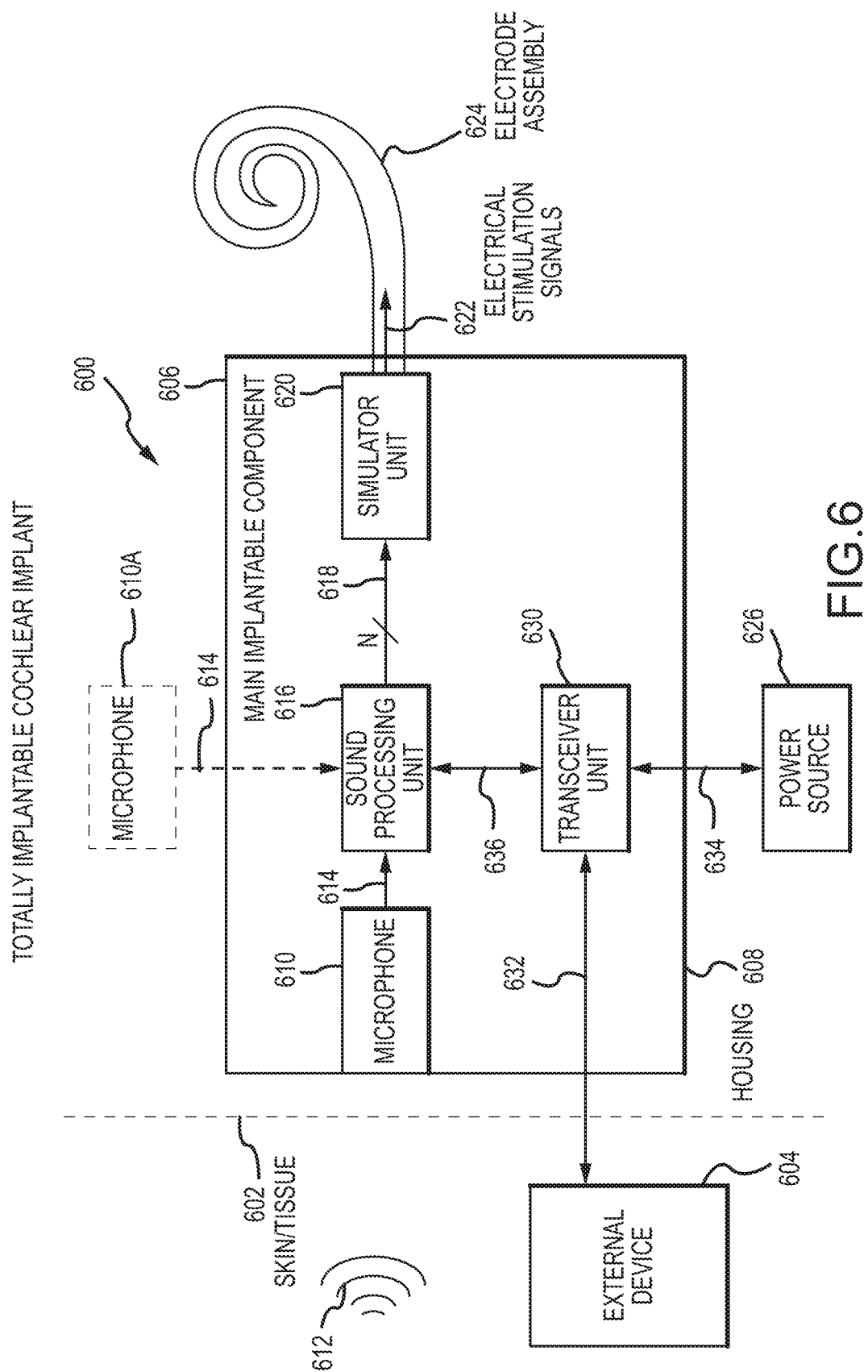
FIG. 6 is a schematic diagram of a totally implantable cochlear implant.

FIG. 6 is a schematic diagram of a totally implantable cochlear implant 600. In a totally implantable cochlear implant 600, all components are configured to be implanted under skin/tissue 602 of a recipient. Because all components of cochlear implant system 600 are implantable, cochlear implant system 600 operates, for at least a finite period of time, without the need of an external device. An external device 604 can be used to charge the internal battery, to supplement the performance of the implanted microphone/system, or for when the internal battery no longer functions. External device 604 can be a dedicated charger or a conventional cochlear implant sound processor. Either way, the external device 604 preferably incorporates a microphone.

As noted, cochlear implant system 600 includes a main implantable component 606 having a hermetically sealed, biocompatible housing 608. The technologies described herein that detect an operational position can be incorporated into either or both of the external device 604 and the main implantable component 606. Disposed in main implantable component 606 is a microphone 610 configured to sense a sound signal 612. Microphone 610 can include one or more components to pre-process the microphone output. As an alternative, the microphone and other aspects of the system can be included in an upgrade or tethered module as opposed to in a unitary body as shown in FIG. 6. For example, a remote microphone 610a tethered to the main implantable component 606 can be utilized.

An electrical signal 614 representing sound signal 612 detected by microphone 610, 610a is provided from the microphone 610, 610a to sound processing unit 616. Sound processing unit 616 implements one or more speech processing and/or coding strategies to convert the pre-processed microphone output into data signals 618 for use by stimulator unit 620. Stimulator unit 620 utilizes data signals 618 to generate electrical stimulation signals 622 for delivery to the cochlea of the recipient. In the example of FIG. 6, cochlear implant system 600 comprises stimulating lead assembly 624 for delivering stimulation signal 622 to the cochlea.

Cochlear implant system 600 also includes a rechargeable power source 626. Power source 626 can comprise, for example, one or more rechargeable batteries. As described below, power is received from an external device, such as external device 604, and is stored in power source 626. The power can then be distributed to the other components of cochlear implant system 600 as needed for operation.

Main implantable component 606 further comprises a control module 628. Control module 628 includes various components for controlling the operation of cochlear implant 600, or for controlling specific components of cochlear implant system 600. For example, controller 628 can control the delivery of power from power source 626 to other components of cochlear implant system 600. For ease of illustration, main implantable component 606 and power source 626 are shown separate. However, power source 626 can alternatively be integrated into a hermetically sealed housing 606 or part of a separate module coupled to component 606. Magnetic sensors (not shown) are operatively connected to the control module 628 and are described further herein (e.g., sensor 330).

As noted above, cochlear implant system 600 further comprises a receiver or transceiver unit 630 that permits cochlear implant system 600 to receive and/or transmit signals 632 to the external device 604. For ease of illustration, cochlear implant system 600 is shown having a transceiver unit 630 in main implantable component 606. In alternative arrangements, cochlear implant system 600 includes a receiver or transceiver unit which is implanted elsewhere in the recipient outside of main implantable component 606.

Transceiver unit 630 is configured to transcutaneously receive power and/or data 632 from external device 604. Power 634 can also be transferred to and from the transceiver unit 630 to charge the power source 626. Signals 636 (power, data, or otherwise) can also be sent to/from the transceiver 630, the sound processing unit 616, and other components of the device as required or desired. As used herein, transceiver unit 630 refers to any collection of one or more implanted components which form part of a transcutaneous energy transfer system. Further, transceiver unit 630 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data 632 from external device 604 to the main implantable component 606.

As noted, transceiver unit 630 receives power and/or data 632 from external device 604. In the illustrative arrangement of FIG. 6, external device 604 comprises a power source (not shown) disposed in an off the ear processor, which is held in place on the recipient's head using any of the foregoing techniques described, e.g., via a magnet (not show) disposed in the external device 604 and another magnet (not shown) disposed in the main implantable component 606. In such embodiments, the external device 604 is able to rotate and shift to some degree during operation and in between cycles of operation of the cochlear implant system 600 and/or external component 604, which can have an impact on a beam forming algorithm in operation on cochlear implant system 600. Further, the presence of the external device 604 can be detected using any of the suitable techniques described herein. Nevertheless, the external device shown in FIG. 6 is merely illustrative, and other external devices can be alternatively used.

While specific types of auditory prostheses have been described herein, one of skill in the art will appreciate that the systems and methods disclosed herein can be performed using other types of auditory prostheses. For example, the aspects described herein can be performed using a hearing aid, middle ear implant, or other device. Other types of devices can also benefit from the aspects disclosed herein such as, for example, headphones, mobile phones, wireless earpieces, etc. Operational positioning can vary depending on the type of device. For example, hearing aids and passive transcutaneous auditory implant lacks a snap coupling or other type of fastener that limits its processor to a range of positions. Thus, the operational positioning of the sound processor for such a device is not so limited in its range of positioning. As such, there can be greater changes to the effective feedback path of such devices than there will be with other in which the sound processor does snap into position, e.g., a percutaneous auditory prosthesis.

Figure 7:
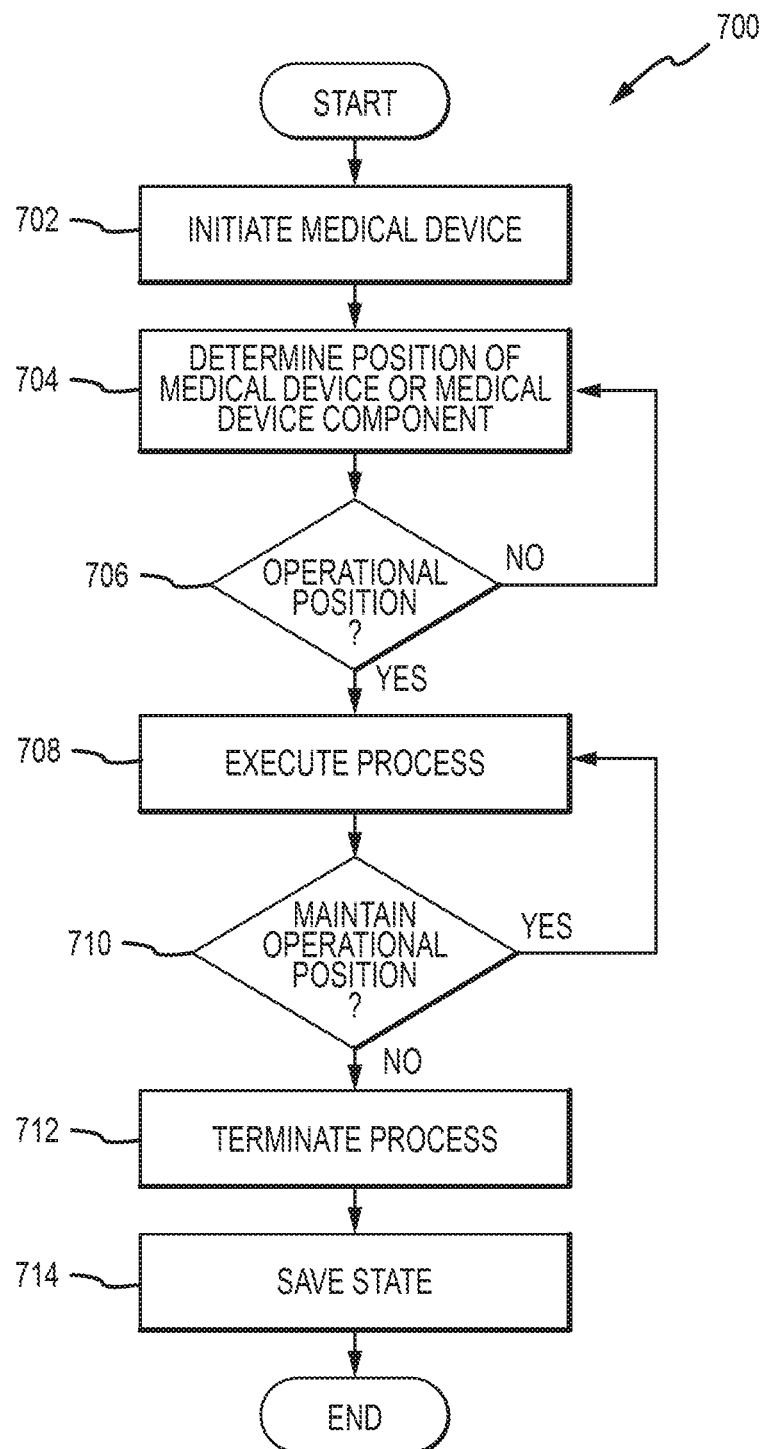
FIG. 7 is an exemplary method for executing a process upon detecting that a device is in an operational position.

Having described various devices that can employ the aspects disclosed herein, the disclosure will now describe various methods for executing processes in an efficient manner. FIG. 7 is an exemplary method 700 for executing a process upon detecting that a device is in an operational position. The method 700 can be implemented using hardware, software, or a combination of hardware and software. In embodiments, the method 700 can be performed by an auditory prosthesis, such as, for example, a bone conduction device, a middle ear device, a hearing aid, etc. The method 700 may also be performed using a general computing device connected to and/or in communication with any of the foregoing. Flow begins at operation 702 where a device is initialized. In one example, initializing a device includes powering on the device. As described above, some processes executed by the device produce better results when the device is in an operational position than they would if the processes were executed before the device is in an operational position. However, in some aspects, while such processes might not complete before the device is in place, parameters can be set upon initialization of the device at operation 702.

After initializing the device, flow continues to operation 704 where a monitoring of the device position is performed. As previously described, aspects disclosed herein relate to performing actions when a device is in an operational position. In examples, an operational position refers to the positioning of a device in a manner that the device is intended to operate in. As an example, an operational position may be a physical location such as the placement of an external sound processor for an implantable auditory prosthesis within proximity of an implanted component, placement of a hearing aid in a recipient's ear canal, placement of a headset on an outer ear, etc. In examples, the determination may be made using various components of a device such as, but not limited to, an external and/or implanted coil, and external and/or implanted magnet, an accelerometer, a gyroscope, a magnetic field sensor, a proximity sensor, a button, a switch, or any other type of component capable of generating information that can be used to determine a physical location of a device. Alternatively, an operational position may refer to placing the device in an operational state such as, for example, establishing a data connection between different operational components of a device. For example, an auditory prosthesis may be considered to be in an operational position upon the establishment of a data link between an external sound processor and an implanted component of the auditory prosthesis, e.g., via external and implanted coils. Flow continues to decision operation 706 where a determination is made as to whether the device is in an operational position. If the device is not in an operational position, flow branches NO and returns to operation 704 where the method continues to monitor the device's position.

If the device is in an operational position, flow branches YES to operation 708. At operation 708 a process is executed. In examples, the process executed at operation 708 is a process that produces improved results, makes better determinations, or provides better outcomes when executed during the correct operational placement of a device. One example of such a process is initialization of a feedback algorithm. Initialization of a feedback algorithm can result in audible artifacts, particularly in systems that include a microphone or other type of input device in the vicinity of an output transducer. When feedback occurs at an auditory prosthesis, the recipient of the auditor prosthesis can experience discomfort. Feedback algorithms combat feedback by cancelling out a feedback signal using an adaptive filter. The settings applied to the adaptive filter have an effect on the feedback reduction. The proper settings can vary depending on the positioning of the device. Because of this, execution of a feedback algorithm provides better results when the execution begins when the device is in an operational positon, which is not necessarily the same instance as when the device is initialized. One of skill in the art will appreciate that various different types of feedback algorithms can be practiced with the various aspects disclosed herein without departing from the spirit or scope of this disclosure. One of skill in the art will appreciate that other types of processes also benefit from beginning execution when a device is in an operational position. For example, a beam forming algorithm may also benefit from executing at the time that a device is placed into an operational position. For instance, beam forming algorithms typically focus on sounds coming from a direction in front of the recipient. If a device is still held in the recipient's hand or otherwise not facing in a proper direction during initialization of the beam forming algorithm, the device might configure itself to reduce as noise speech coming from the direction in front of the recipient. In some embodiments, before the beam forming algorithm is initialized, the microphones of the device are configured to operate in omni directional mode. Changes in gain settings are also better performed when the device is an operational position. In further aspects, the different processes can be executed sequentially or in parallel upon detection that the device is in place. In one example, beam forming can be executed prior to execution of the feedback algorithm. Because directionality can affect the feedback path, if the beam forming is performed before feedback reduction, additional benefits can be gained from the feedback algorithm. While the disclosure describes various different processes executing at operation 708, one of skill in the art will appreciate that other types of processes can be executed at operation 708 without departing from the scope of this disclosure.

Flow continues to decision operation 710 where a determination is made as to whether the device is still in an operational position. As discussed with respect to operation 704, the determination can be based upon the physical location of the device and/or an operating state of a device.

As indicated herein, the device may rotate, shift or move otherwise to some degree and still remain in an/the operational position. Typically, and depending on device type, relatively stability of the feedback path, etc., an auditory prosthesis provides 0-6 dB of additional available gain during a fitting of the prostheses to a recipient. Further, some feedback algorithms with phase shifting provide 10-12 dB of additional gain without artefacts and up to 20 dB of additional gain with some artefacts. This means that in some embodiments, there is between 4-12 dB in feedback algorithm margin. So long as the movement of the device does not consume that margin, the device affectively remains in an/the operational position. Moreover, in some embodiments, the operation of the device might be interrupted temporarily. For instance, a recipient might lean against a wall or interrupt a feedback path between a speaker and a microphone of the device. Such actions could have a negative impact on operation of the device, e.g., consume the margin referred to herein. So long as the interruption is brief, e.g., less than 1 second or within range of some other time, the device remains in the operational position despite the interruption. If the margin is consumed or consumed for a significant period of time, the device in some embodiments treats that as the device no longer being in the operational position even if, for instance, successful communications between external and internal components of the device remain.

If the device is still in an operational position, flow branches YES and returns to operation 708 where the one or more processes continue execution. If the device is no longer in an operational position, flow branches NO to operation 712. At operation 712, one or more processes executed at operation 708 are terminated. In one example, terminating processes provides for an increase in battery life for the device. Energy usage can be minimized by halting the execution of processes that are unnecessary based upon a device's position and/or state. Additionally, halting of the one or more processes prevents the device from transitioning into a sub-optimal or inoperable state. For example, the continuation of certain feedback reduction and/or beam forming algorithms (e.g., ongoing dynamic adjustments) can result in sub-optimal settings being applied to the device due to the fact that the device is no longer in an operational position. For example, feedback and beam forming settings applied when an auditory prosthesis is in the hand of a recipient will not produce optimal results.

Flow then continues to optional operation 714. At optional operation 714, the state or settings of the device at the time the device is removed from the operational position are saved. Saving the state or settings can include saving any parameters or settings generated using one or more processes executed at operation 708. Saving the state or settings allows for the initialization of the device to the functional state or settings when the device was last in an operational position. This can lead to an enhanced experience for the recipient when the device is again placed into operation, e.g., less aggressive settings during initialization of the feedback algorithm.

Figure 8:
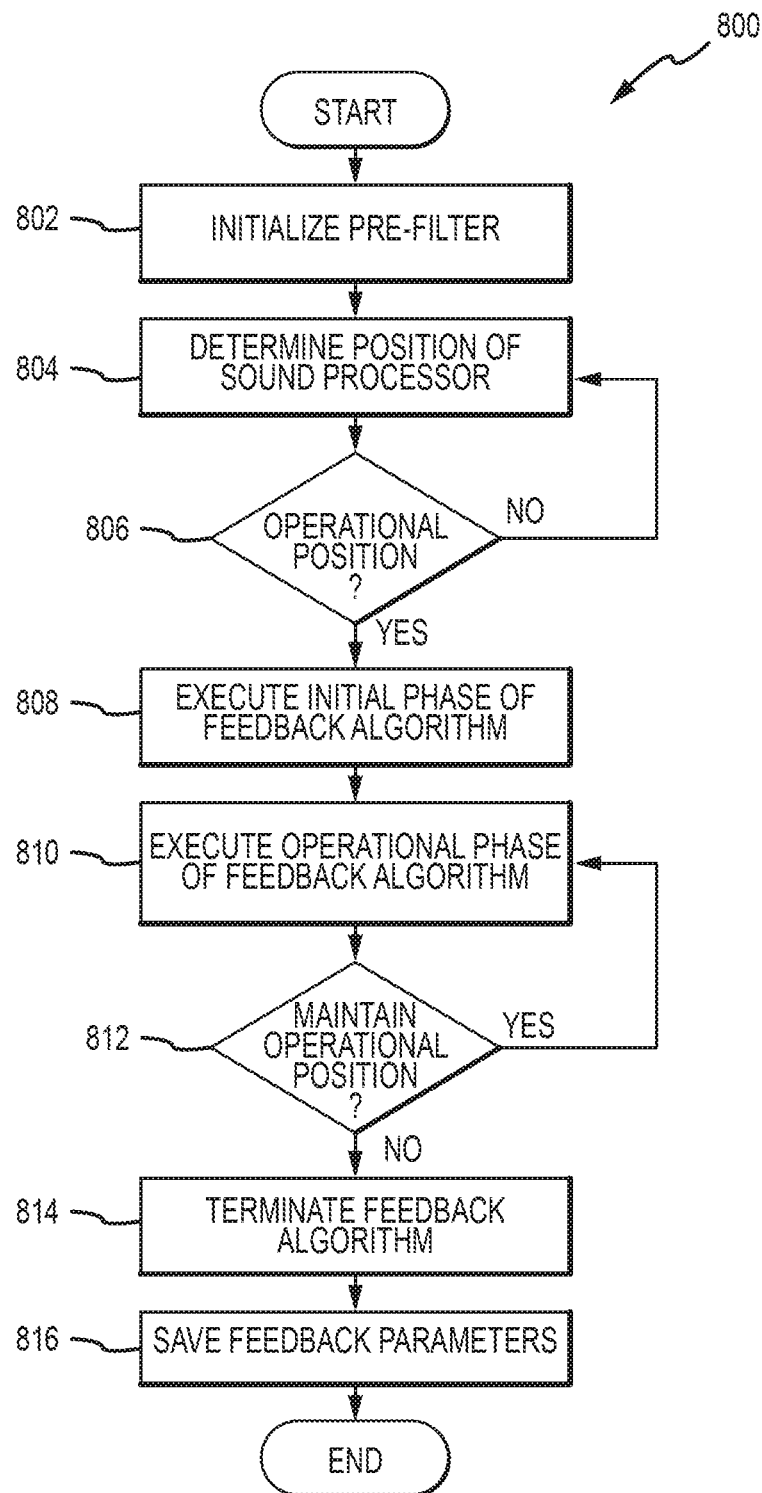
FIG. 8 is an exemplary method for executing a feedback algorithm upon detecting that a sound processor is in an operational position.

FIG. 8 is an exemplary method 800 for executing a feedback algorithm upon detecting that a sound processor of an auditory prosthesis is in an operational position. The method 800 can be implemented using hardware, software, or a combination of hardware and software. In embodiments, the method 800 can be performed by an auditory prosthesis, such as, for example, a bone conduction device, a middle ear device, a hearing aid, etc. The method 800 may also be performed using a general computing device connected to and/or in communication with the foregoing devices. Flow begins at operation 802 where a pre-filter may be set for a feedback algorithm. In examples, the pre-filter may be settings that were determined during a previous fitting process for the device. In further examples, the pre-filter may be settings that were in place the last time that the device was in an operational position. In further embodiments, other parameters may be set at operation 802. For example, parameters related to step-size for gain increase, frequency parameters depending upon air delay, filter dynamics, etc. may be set at operation 802. Setting a pre-filter at operation 802 allows the feedback algorithm to employ slower adaptation than is possible at a later stage (e.g., at operation 808). Slower adaptation reduces the risk of instability and reduces the chance that audible artifacts occur, thereby enhancing the recipient's experience.

Flow continues to operation 804 where monitoring of the position of the sound processor is performed. The monitoring is performed to determine whether the sound processor is in an operational position. In one example, the sound processor may be in an operational position when the sound processor is in a substantially fixed location that is expected while the device remains in operation. In one example, the sound processor may be in a substantially fixed location based upon a locational relationship of the sound processor with respect to another component of the auditory prosthesis, with respect to the recipient, or with respect to both. In other aspects, an operational position may be defined by a substantially fixed feedback path that is expected while the device is in an operational position. In still other aspects, the operational position may be defined by feedback settings. For example, the sound processor may be in an operational position when it is determined that the current feedback settings are settings that tend to be consistent from one instance of operation to the next. In one example, the sound processor can be determined to be in an operational position based upon a coil-on event. That is, if the external and internal coils of the sound processor are within proximity to one another and/or upon the establishment of a data link between the coils, then it can be determined that the sound processor is in an operational position. In an alternate embodiment, the determination of the operational position can be based upon the proximity of internal and external magnets of the auditory prosthesis. When the internal and external magnets are in a close proximity, then the sound processor can be determined to be in an operational position.

Flow continues to decision operation 806 where a determination is made as to whether the sound processor is in an operational position based upon the monitoring performed at operation 804. If it is determined that the device is not in an operational position, flow branches NO and returns to operation 804 where continued monitoring of the sound processor's position is performed. If the sound processor is determined to be in an operational position, flow branches YES to operation 808. At operation 808, an initial phase of a feedback algorithm is executed. In examples, the initial phase of the feedback algorithm can have a first adaptation speed. The first adaptation speed can be more aggressive, e.g., faster, than an operational adaptation speed. In examples, it is beneficial to apply a more aggressive adaptation speed during the initial phase to quickly identify and set optimal settings for the sound processor. However, faster adaptation speeds increase the likelihood of audible artifacts. As will be discussed in further detail with respect to FIG. 9, certain mechanisms can be employed to reduce the likelihood of such artifacts during the initial phase. Further, the relative stability of the feedback path, which depends in part on device type, can be used to configure/select the first and/or second adaptation speeds and adjust or set other settings or characteristics during an initialization and/or operational phase of a feedback or other algorithm. For instance, the first adaptation speed can be relatively slower for devices with a relatively stable feedback path.

After the initial phase has completed, flow continues to operation 810 where an operational phase of the feedback algorithm is executed. In one example, the initial phase can be completed after a set amount of time. Alternatively, the initial phase can be completed upon reaching a certain state or collection of settings. For example, the initial phase can be completed upon reaching a stable feedback loop, that is, upon reaching a consistent state or collection of settings for the feedback algorithm. During the operational phase, the adaptation speed of the feedback algorithm may be reduced, that is, a less aggressive adaptation speed can be applied. It is possible to reduce the adaptation speed because a stable feedback loop can be in place during the operational phase partly through the use of a properly configured and timed initial phase. The slower adaption speed reduces the likelihood of audible artifacts during the operation of the sound processor.

After entering the operational phase, flow continues to decision operation 812. At decision operation 812, a determination is made as to whether the sound processor is still in the operational position. The determination can be made according to the various examples described with respect to operations 804 and 806. If the sound processor is still in an operational position, flow branches YES and returns to operation 810 where the operational phase of the feedback algorithm continues to execute. However, if the sound processor is no longer in an operational position, then flow branches NO to operation 814. At operation 814, the execution of the feedback algorithm is terminated. Because the sound processor is no longer in an operational position, any adjustments made by the feedback algorithm may result in sub-optimal performance. In other words, any adjustments made after the sound processor is no longer in an operational position can be invalid.

After terminating execution of the feedback algorithm, flow continues to optional operation 816. At optional operation 816, parameters and or settings in place at the time the sound processor was in operational position can be saved. Saving the parameters and or settings allows for the initialization of the sound processor to the saved parameters and or settings. For example, the settings saved at operation 814 can be applied during the initialization operation 802 the next time the sound processor is activated. This allows for the sound processor to more efficiently and/or less aggressively reach a stable feedback loop, which, in turn, reduces the likelihood of audible artifacts.

Figure 9:
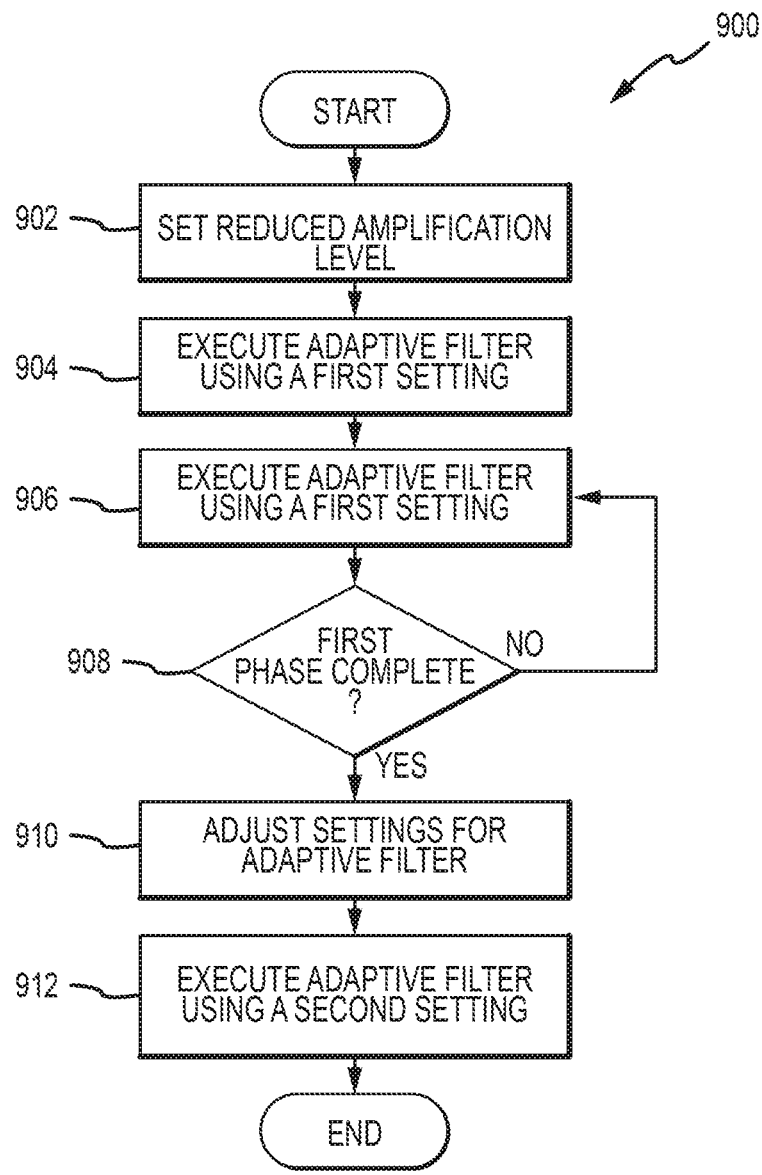
FIG. 9 is an exemplary method for performing phased feedback reduction.

FIG. 9 is an exemplary method 900 for performing phased feedback reduction. The method 900 can be implemented using hardware, software, or a combination of hardware and software. In embodiments, the method 900 can be performed by an auditory prosthesis, such as, for example, a middle ear device, a bone conduction device, a hearing aid, etc. The method 900 can also be performed using a general computing device. In examples, the method 900 can be performed during operations 508 and 510 of the method 500. Flow begins at operation 902 where a reduced amplification level setting is applied. Reduction of the amplification setting can reduce the likelihood of audible artifacts occurring during initialization of a feedback algorithm. In examples, in addition to setting a reduced amplification setting, an amplification step can be set at operation 902. The amplification step defines how quickly the amplitude of the auditory prosthesis can be altered. For example, an amplification step of 5 dB can be set. Under such circumstances, the amplification of the auditory prosthesis can be adjusted in 5 dB increments. Other step sizes can be set without departing from the spirit of this disclosure.

Flow continues to operation 904 where a feedback algorithm is executed with a first adaptation speed. In examples, the operation 902 can be performed at the initialization of the feedback algorithm. Because the algorithm is just initialized, the feedback loop is more likely to be unstable. Because of this, a faster adaptation speed can be employed to quickly stabilize the feedback loop. The first adaptation speed can be faster, e.g., more aggressive. Because a reduced amplification level was set at operation 902, the likelihood of audible artifacts is reduced during execution of the aggressive adaptation speed. Flow continues to operation 906 where the amplification level is adjusted by an amplification step size. In this manner, the amplification level of the auditory prosthesis can be incrementally brought to an operational amplification setting while continuing to perform aggressive feedback reduction. The incremental increase reduces the likelihood of generating an audible artifact. The amplification step size can be determined by a prior setting, for example, by a level determined during operation 902. Alternatively, the amplification step size can be dynamically determined based upon the status of the feedback loop.

Flow continues to decision operation 908 where a determination is made as to whether the initial phase of the feedback algorithm has completed. In one example, the initial phase can be completed after a set amount of time. Alternatively, the initial phase can be completed upon reaching a certain state or collection of settings. For example, the initial phase can be completed upon reaching a stable feedback loop, that is, upon reaching a consistent state or consistent settings for the feedback algorithm. If the feedback algorithm is still in the initial phase, flow branches NO and returns to operation 906 where the amplification is adjusted again by a step size and the feedback algorithm continues to operate at a faster adaptation speed. If the initial phase has completed, flow branches YES to operation 910.

At operation 910, the adaptation speed of the feedback algorithm is reduced, e.g., a less aggressive adaptation speed is applied. The slower adaption speed reduces the likelihood of audible artifacts during the operation of the sound processor. Flow then continues to operation 912 where the feedback algorithm continues to operate at the reduced adaptation speed.

Figure 10:
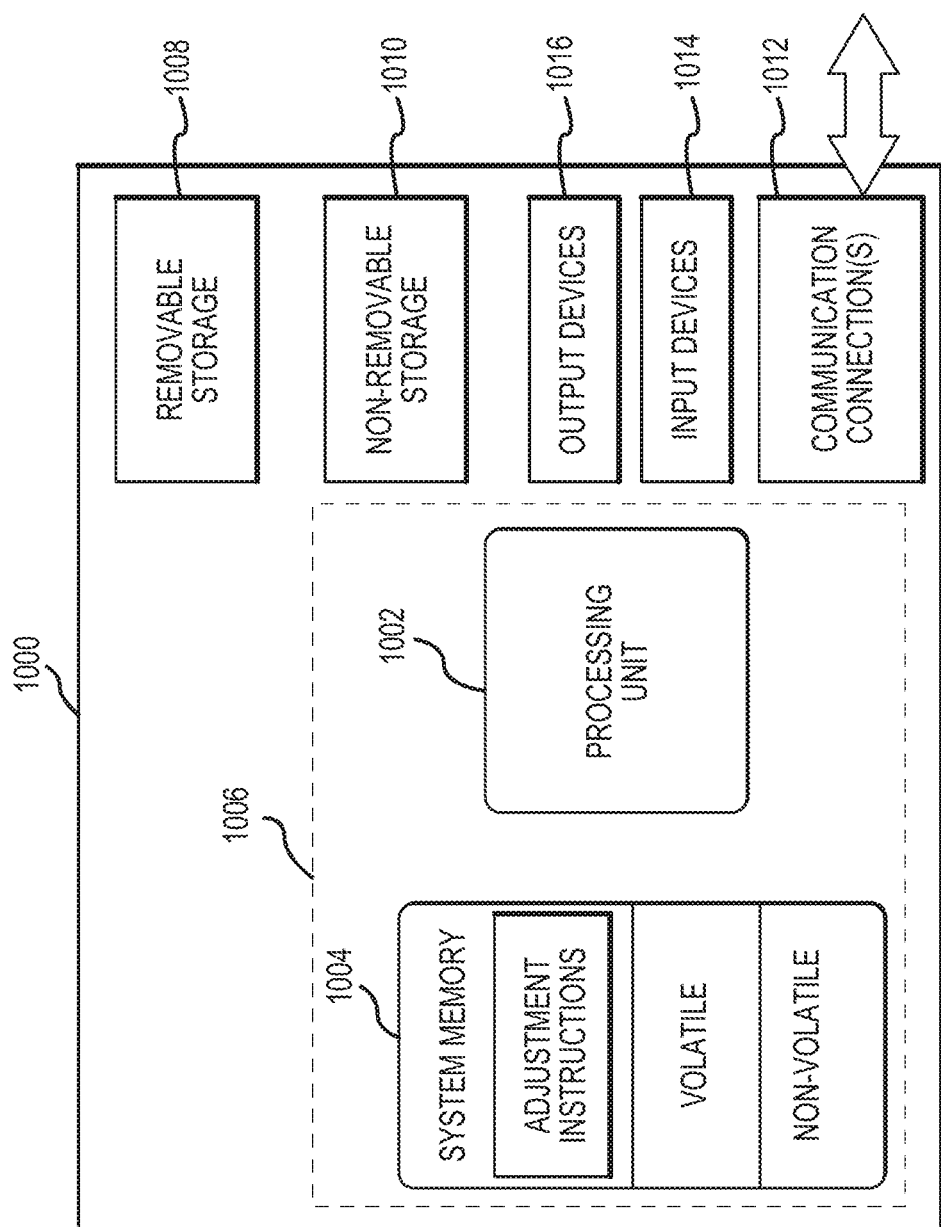
FIG. 10 illustrates one example of a suitable operating environment in which one or more of the present examples can be implemented.

FIG. 10 is an embodiment of a system 1000 in which the various systems and methods disclosed herein can operate. The most basic components of the system 1000 may be included as part of an auditory prosthesis. In alternate embodiments, a client device in communication with the auditory prosthesis, can be employed to set and/or perform the feedback algorithms and other processes disclosed herein. In such embodiments, a client device, such as client device 1002, can communicate with one or more auditory prostheses, such as auditory prosthesis 1004, via a network 806. In embodiments, a client device can be a remote control, a laptop, a personal computer, a smart phone, a PDA, a netbook, a tablet computer, a server or any other type of computing device, such as the computing device in FIG. 10. In embodiments, the client device 1002 and the auditory prosthesis 1004 may communicate via communication channel 1006. Communication channel 1006 can be any type of network capable of facilitating communications between the client device 1002 and the auditory prosthesis 1004. Examples of a communication channel can be an RF connection, a Bluetooth connection, a WiFi connection, or any other type of connection capable of transmitting instructions between client device 1002 and auditory prosthesis 1004.

In embodiments, the various systems and methods disclosed herein can be performed by an auditory prosthesis, e.g., auditory prosthesis 1004, a client device, e.g., client device 1002, or by both the auditory prosthesis and client device. For example, in embodiments the client device may perform a method to identify a control expression and instruct the auditory prosthesis to apply an audio setting adjustment. In such embodiments, client device 1002 can transmit instructions to the auditory prosthesis to apply an audio setting instruction via communication connection 1006.

Communication channel 1006, in certain embodiments, is capable of real-time or otherwise suitably fast transmission of, e.g., instructions from client device 1002 to auditory prosthesis 1004. In such embodiments, instructions from the client device 1002 based on its processing of a control expression and related conversation is received in good time by the auditory prosthesis 1004. If, for instance, such instructions are not transmitted suitably fast, an audio setting adjustment to auditory prosthesis 1004 might not be made in time benefit the recipient (e.g., in time for the repeat of a conversation fragment the recipient requested with the control expression).

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. A method comprising:
   determining if a device for an auditory prosthesis is in an operational position; and
   when the device is in the operational position, executing an algorithm to reduce the likelihood of an auditory artifact,
   wherein the algorithm comprises a plurality of feedback algorithms, and the method further comprises applying a first feedback algorithm of the plurality of feedback algorithms during a first phase and a second feedback algorithm of the plurality of feedback algorithms during a second, operational phase, wherein the first feedback algorithm provides quicker adaptation than the second feedback algorithm.

2. The method of claim 1, further comprising, prior to determining if the device is in the operational position, preconfiguring the device.

3. The method of claim 2, wherein preconfiguring the device comprises setting a pre-filter for the algorithm.

4. The method of claim 2, wherein preconfiguring the device comprises adjusting at least one setting for the device to match at least one setting determined during a fitting process of the auditory prosthesis.

5. The method of claim 2, wherein preconfiguring the device comprises adjusting at least one setting to match at least one setting determined when the device was previously in the operational position.

6. The method of claim 1, wherein determining that the device is in the operational position comprises detecting an established data link with at least one other component of the auditory prosthesis.

7. The method of claim 1, wherein the device is an external sound processor, and wherein determining that the device is in the operational position comprises detecting that the external sound processor is in proximity of an implanted magnet.

8. The method of claim 1, further comprising:
   determining if the device for the auditory prosthesis is not in the operational position.

9. The method of claim 8, further comprising:
   storing at least one setting for the device determined a feedback algorithm when the device was in the operational position for use when the device returns to the operational position.

10. The method of claim 1, wherein the algorithm is a beam forming algorithm.

11. The method of claim 1, wherein the actions of determining and the actions of executing are executed by the auditory prosthesis that provides a mechanical output to tissue of a recipient thereof to evoke a hearing percept.

12. The method of claim 1, wherein the actions of determining and the actions of executing are executed by the auditory prosthesis which does not include a beamforming feature.

13. A method comprising:
   determining if a device for an auditory prosthesis is in an operational position;
   when the device is in the operational position, executing an algorithm to reduce the likelihood of an auditory artifact;

determining if the device for the auditory prosthesis is not in the operational position; and altering operation of a feedback algorithm in response to determining that the device is not in the operational position.

14. The method of claim 13, wherein the algorithm includes a plurality of phases.

15. The method of claim 14, wherein the plurality of phases comprises an initial phase lasting a first period of time.

16. The method of claim 15, further comprising applying a first feedback algorithm during the initial phase.

17. The method of claim 15, further comprising:
at the start of the initial phase, setting an amplification of the device to a reduced level; and
incrementally increasing the amplification level during the initial phase.

18. The method of claim 16, wherein the plurality of phases comprises an operational phase.

19. The method of claim 18, further comprising applying a second feedback algorithm during the operational phase, wherein the second feedback algorithm employs a lower adaptation speed than the first feedback algorithm.

20. The method of claim 13, wherein the actions of determining and the actions of executing are executed by the auditory prosthesis that includes a beamforming feature, wherein the auditory artifact is unrelated to beamforming.

21. The method of claim 13, wherein the auditory artifact is a chirp or a tone, and wherein the methods of determining and executing are executed by the auditory prosthesis.

22. A method comprising:
determining if a device for an auditory prosthesis is in an operational position; and
when the device is in the operational position, executing an algorithm to reduce the likelihood of an auditory artifact,
wherein the actions of determining and the actions of executing are executed by the auditory prosthesis which is a mechanical output hearing prosthesis.

23. The method of claim 22, wherein the device is an external sound processor, and wherein determining that the device is in the operational position comprises detecting that the external sound processor is snapped on to a percutaneous abutment.

24. The method of claim 22, wherein during the action of determining and during the action of executing, a feedback reduction algorithm of a hearing prosthesis which is executing the action of determining and executing the action of executing is operating to reduce feedback.

25. The method of claim 22, wherein the algorithm comprises a feedback algorithm and a plurality of phases, wherein the method further includes:
at a start of an initial phase of the plurality of phases, setting an amplification of the device to a reduced level; and
incrementally increasing the amplification level during the initial phase.

26. The method of claim 22, wherein the algorithm comprises a plurality of feedback algorithms, and the method further comprises applying a first feedback algorithm of the plurality of feedback algorithms during a first phase and a second feedback algorithm of the plurality of feedback algorithms during a second, operational phase, wherein the first feedback algorithm provides quicker adaptation than the second feedback algorithm.

27. The method of claim 22, wherein the algorithm is a feedback reduction algorithm that is less aggressive than a previously operated feedback reduction algorithm.

28. The method of claim 22, wherein the algorithm is a feedback reduction algorithm that is operating while a beamforming algorithm, separate from the algorithm, is also operating.

29. The method of claim 22, wherein the auditory prosthesis is a bone conduction hearing prosthesis.

30. A method comprising:
determining if a device for an auditory prosthesis is in an operational position; and
when the device is in the operational position, executing an algorithm to reduce the likelihood of an auditory artifact,
wherein the algorithm sets an amplification of the device to a reduced level at a first time period and then incrementally increases the amplification level during a second time period after the first time period.

31. The method of claim 30, wherein the algorithm comprises a feedback algorithm and a plurality of phases, wherein the method further includes:
at a start of an initial phase of the plurality of phases, setting an adaptation speed of the feedback algorithm at a first level; and
determining that the initial phase should be completed, and upon such completion, setting the adaptation speed of the feedback algorithm at a second level such that the adaptation speed of the feedback algorithm is reduced relative to that at the first level.

* * * * *